United States Patent
Bae et al.

(10) Patent No.: US 7,437,908 B2
(45) Date of Patent: Oct. 21, 2008

(54) PARTICLE COUNTER

(75) Inventors: Gwi-Nam Bae, Seoul (KR); Kil-Choo Moon, Seoul (KR); Seung-Bok Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 392 days.

(21) Appl. No.: 11/354,984

(22) Filed: Feb. 16, 2006

(65) Prior Publication Data
US 2007/0056395 A1    Mar. 15, 2007

(30) Foreign Application Priority Data
Sep. 15, 2005   (KR) .................... 10-2005-0086079

(51) Int. Cl.
*G01N 15/12*    (2006.01)
*G01N 15/02*    (2006.01)

(52) U.S. Cl. .................. 73/28.02; 73/28.04; 73/865.5; 324/71.4

(58) Field of Classification Search ............... 73/28.02, 73/28.04, 865.5; 324/71.4
See application file for complete search history.

(56) References Cited

U.S. PATENT DOCUMENTS

| | | | | |
|---|---|---|---|---|
| 3,419,718 A | * | 12/1968 | Hammond et al. | 250/251 |
| 3,449,667 A | * | 6/1969 | Gourdine | 324/71.1 |
| 3,679,973 A | * | 7/1972 | Smith et al. | 73/28.02 X |
| 3,740,149 A | * | 6/1973 | Whetten | 356/335 |
| 3,953,792 A | * | 4/1976 | Fletcher et al. | 324/71.4 |
| 6,040,574 A | * | 3/2000 | Jayne et al. | 250/288 |
| 6,263,744 B1 | * | 7/2001 | Russell et al. | 73/865.5 |
| 6,639,671 B1 | * | 10/2003 | Liu | 356/336 |
| 6,892,142 B2 | * | 5/2005 | Takeuchi et al. | 702/23 |
| 7,100,423 B2 | * | 9/2006 | Trenholm | 73/28.02 |
| 2003/0202920 A1 | * | 10/2003 | Kaufman et al. | 422/186 |
| 2005/0179893 A1 | * | 8/2005 | Hill | 356/318 |
| 2007/0131038 A1 | * | 6/2007 | Wei et al. | 73/865.5 |

FOREIGN PATENT DOCUMENTS

EP      416472 A2 * 3/1991

(Continued)

OTHER PUBLICATIONS

Proceeding of the 2005 Korean Society for Atmospheric Environment (May 10, 2005), "Electrical Measurement of Particles Grown by Condensation", Abstract. 8 pages (Translation page, cover page, indexing page, p. 25, pp. 326-327 , drawing pp. 1-2).

*Primary Examiner*—Thomas P Noland
(74) *Attorney, Agent, or Firm*—Browdy and Neimark, P.L.L.C.

(57) ABSTRACT

A particle counter has a saturator inhaling air in an atmosphere and vaporizing a working liquid therein; and an electrical detection unit electrically shielding an internal space thereof to maintain a temperature of the space to be constant, the air and vaporized working liquid flowing into the electrical detection unit through a side thereof from the saturator, condensing the vaporized working liquid on surfaces of ultrafine particles contained in the air, and charging the particles to measure a current of the charged particles, thereby measuring the number of the particles included in the air. According to the invention, it is possible to measure the number concentration of the ultrafine particles included in the air, and it is easy to move the counter depending on the measurement locations.

13 Claims, 7 Drawing Sheets

FOREIGN PATENT DOCUMENTS

| | | | | |
|---|---|---|---|---|
| EP | 1102055 A2 | * | 5/2001 | |
| GB | 2243447 A | * | 10/1991 | ................ 73/28.04 |
| GB | 2340225 A | * | 2/2000 | |
| JP | 05312710 | * | 11/1993 | |
| KR | 2005053194 A | * | 6/2005 | |
| SU | 1603244 A1 | * | 10/1990 | |

* cited by examiner

PARTICLE COUNTER

BACKGROUND OF THE INVENTION

1. Field of the Invention

The present invention relates to a particle counter, and more particularly to a particle counter capable of counting a number concentration of ultrafine particles by condensing a vaporized working liquid on the surfaces of ultrafine particles to grow them, charging ions on the grown micro particles and then measuring an amount of the ions.

2. Description of the Prior Art

In recent years, it has been very important to measure a number concentration of ultrafine particles when closely examining phenomena of photochemical smog, visibility, atmospheric chemical reaction and the like or evaluating an toxicity of ultrafine particles deeply inhaled in human lungs through a breathing, in fields of atmospheric environments. In addition, the importance of the measurement is further emphasized in a variety of industrial applications such as analysis of physicochemical properties of ultrafine particles, semiconductor field, particle control of nano-industry field and the like.

An equipment of measuring a number concentration of particulate matters including ultrafine particles may be classified into an equipment of using an optical sensor to measure the number of particles and an equipment of charging particles to measure a current.

The equipment using the optical sensor includes a wide range particle spectrometer (WPS) available from MSP company, a condensation nucleus counter (CNC) of Met One company, a condensation particle counter (CPC) constituting a scanning mobility particle sizer (SMPS) of TSI company, a laser particle counter (LPC) available from PMS company and the like. In addition, the equipment using the electrical measuring method includes, for example an electrical low pressure impactor (ELPI) available from Dekati company.

The CPC of TSI company widely used among the equipments using the optical sensor for measurement vaporizes alcohol, condenses the vaporized alcohol on surfaces of ultrafine particles to enlarge the particles and then optically measures a number concentration of the particles. However, the equipments using the optical sensor to measure the number concentration of ultrafine particles, including the CPC, are very expensive and the optical sensor is liable to be contaminated by working liquid while they are moved to other measurement places.

In addition, the ELPI using the electrical method charges wide-range particles to the utmost and then measures charge quantity of the charged particles, thereby measuring the number concentration of the particles. In this case, the maximal charge quantity capable of being retained by the particle is determined by a size of the particle. Although a spherical particle having a diameter of 1 $\mu$m can contain approximately 156,000 electrons, the charge quantity is highly different depending on methods of charging the particles. In general, when a number concentration of the particles uniformly charged with about 1,000 charges is 100 particles/cm$^3$ and a flow rate of 1 l/min is allowed to pass through an ammeter, i.e., 1×10$^5$ particles per minute pass through an ammeter, a current to be detected is about 2.7×10$^{31\ 13}$ A. Accordingly, the measured current can be transformed into a number concentration of the particles.

When such electrical method is used, there is not occurred the contamination problem as for the optical sensor during the movement. However, since a lower limit of measurable particle is about 0.03 $\mu$m, it is possible to measure only a particle having a relatively large diameter compared to the equipment using the optical sensor. The reason is that since the smaller the size of the particle, the less the charge quantity charged to the surface of the particle, there is limitation in a measurable low electric signal. Accordingly, the electrical measurement of a number concentration of particles has disadvantage in accuracy, compared to the equipment using the optical sensor.

SUMMARY OF THE INVENTION

Accordingly, the present invention has been made to solve the above problems. An object of the invention is to provide a particle counter capable of freely moving and measuring a number concentration of smaller particles, compared to an equipment using the prior electrical method.

In order to achieve the above object, there is provided a particle counter comprising: a saturator inhaling air in an atmosphere and vaporizing a working liquid therein; and an electrical detection unit electrically shielding an internal space thereof to maintain a temperature of the space to be constant, the sampled air with the vaporized working liquid flowing into the electrical detection unit through a side thereof from the saturator, condensing the vaporized working liquid on surfaces of ultrafine particles contained in the air, and charging the particles to measure a current of the charged particles, thereby measuring the number of the particles included in the air.

According to an embodiment of the invention, the electrical detection unit may comprise a housing having an inlet through which the air with vaporized working liquid supplied from the saturator flows in and an inside to be electrically shielded; a low temperature regulator maintaining an inside temperature of the housing to be lower than that of the saturator inside and thus allowing the working liquid vaporized in the saturator to be condensed on the surfaces of the ultrafine particles included in the air; a charging section formed in the housing and charging the micro particles having the working liquid condensed thereon; and a current measuring section formed in the housing and measuring a charge quantity of the micro particles charged by the charging section.

According to a preferred embodiment of the invention, the charging section may preferably comprise a plurality of electrodes protruding from an inner wall of the housing toward a center thereof; and a high voltage power supply applying a voltage to the electrodes. Many ions are generated in the housing by a corona discharge of the electrodes by the high voltage applied from the high voltage power supply and the micro particles having the working liquid condensed thereon are charged by the ions.

In the mean time, according to an embodiment of the invention, the particle counter may further comprise an ion removing section removing residual ions that are not charged on the micro particles in the air, between the charging section and the current measuring section.

According to an embodiment of the invention, the ion removing section may comprise a voltage power supply mounted to a side of the housing; an ion trap electrode located in the center of the housing and generating electric field by the voltage power supply to push the ions that are not charged on the micro particles, toward the inner wall of the housing by an electric force; and an ion removing wall mounted to the inner wall of the housing and removing the ions having been pushed toward the inner wall of the housing.

According to an embodiment of the invention, the current measuring section may comprise a conductive filter collecting the charged particles to separate the ions and the particles from each other; a support member and a fixing member for supporting the conductive filter; and a current measuring device measuring a current of the ions retained on the charged particles collected by the conductive filter and displaying the measured current with a computer.

In the mean time, according to another embodiment of the invention, the particle counter may further comprise a flow splitter inhaling the air in the atmosphere to split an amount of the air just enough to be used for the measurement, and then supplying the split air to the saturator and discharging the residual air through a passage for vent line; and a flow rate regulating unit regulating a flow rate of the air supplied to the saturator through the flow splitter and a flow rate of the air discharged through vent line.

In addition, according to an embodiment of the invention, the particle counter may further comprise a particle separating unit separating particles having sizes rather than a size to be measured in the air split by the flow splitter between the flow splitter and the saturator.

Meanwhile, according to an embodiment of the invention, the particle counter may further comprise a diluting device inhaling air in the atmosphere to dilute the number concentration of ultrafine particles contained in the air and supplying the diluted air to the flow splitter.

BRIEF DESCRIPTION OF THE DRAWINGS

The above and other objects, features and advantages of the present invention will be more apparent in the following detailed description taken in conjunction with the accompanying drawings, in which.

DETAILED DESCRIPTION OF THE PREFERRED EMBODIMENTS

Hereinafter, a preferred embodiment of the present invention will be described with reference to the accompanying drawings. In the following description of the present invention, a detailed description of known functions and configurations incorporated herein will be omitted when it may make the subject matter of the present invention rather unclear.

Figure 1:
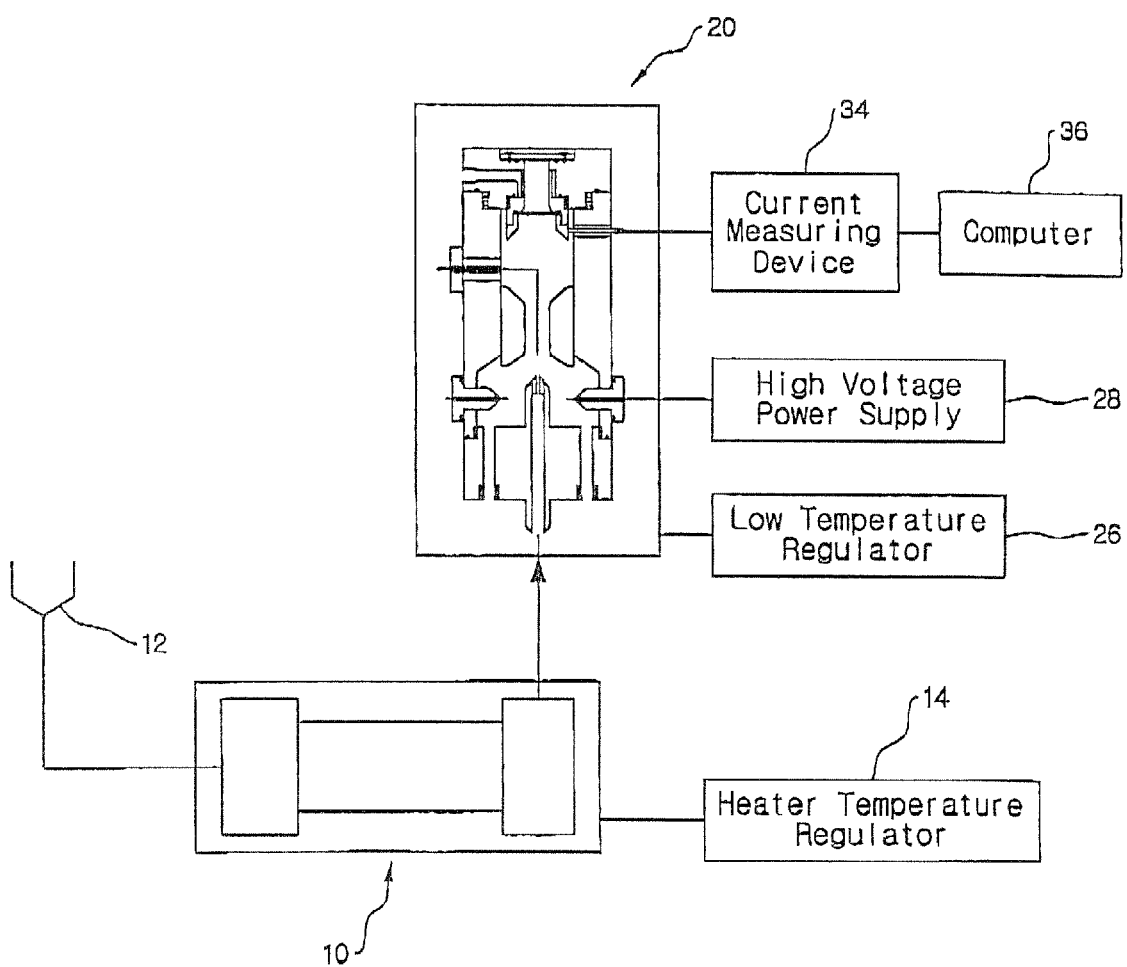
FIG. 1 is a schematic view showing a structure of a particle counter according to a preferred embodiment of the invention.

FIG. 1 is a schematic view showing a structure of a particle counter according to an embodiment of the invention.

Referring to FIG. 1, a particle counter according to an embodiment of the invention comprises a saturator 10 inhaling air in an atmosphere and vaporizing a working liquid therein; and an electrical detection unit 20 electrically shielding an internal space thereof to maintain a temperature of the space to be constant, condensing the working liquid vaporized in the saturator 10 on surfaces of ultrafine particles to enlarge a volume of the particles, and charging the grown micro particles to measure a charge quantity of the charged particles.

The saturator 10 comprises an air inlet 12 through which the air in the atmosphere flows in and a heater temperature regulator 14 maintaining an internal space of the saturator 10 to be a predetermined temperature. When the air flows in the saturator 10 through the air inlet 12, the heater temperature regulator 14 regulates the internal temperature of the saturator 10 to vaporize the working liquid whose vapor will be condensed on surfaces of the ultrafine particles. Although alcohol is used as the working liquid in a preferred embodiment of the invention, it should be noted that the invention is not limited thereto and suitable working liquids can be employed by those skilled in the art.

Although not shown in Figs., the saturator 10 is connected to a separate working liquid tank and supplied with the working liquid from the tank. Some of the vaporized working liquid is condensed on the surfaces of the ultrafine particles in the saturator 10. However, most of the working liquid is not condensed due to the high internal temperature of the saturator 10 and exists as a vapor state. Like this, the vaporized working liquid, air and ultrafine particles are allowed to flow in the electrical detection unit 20 which will be later described.

Figure 2:
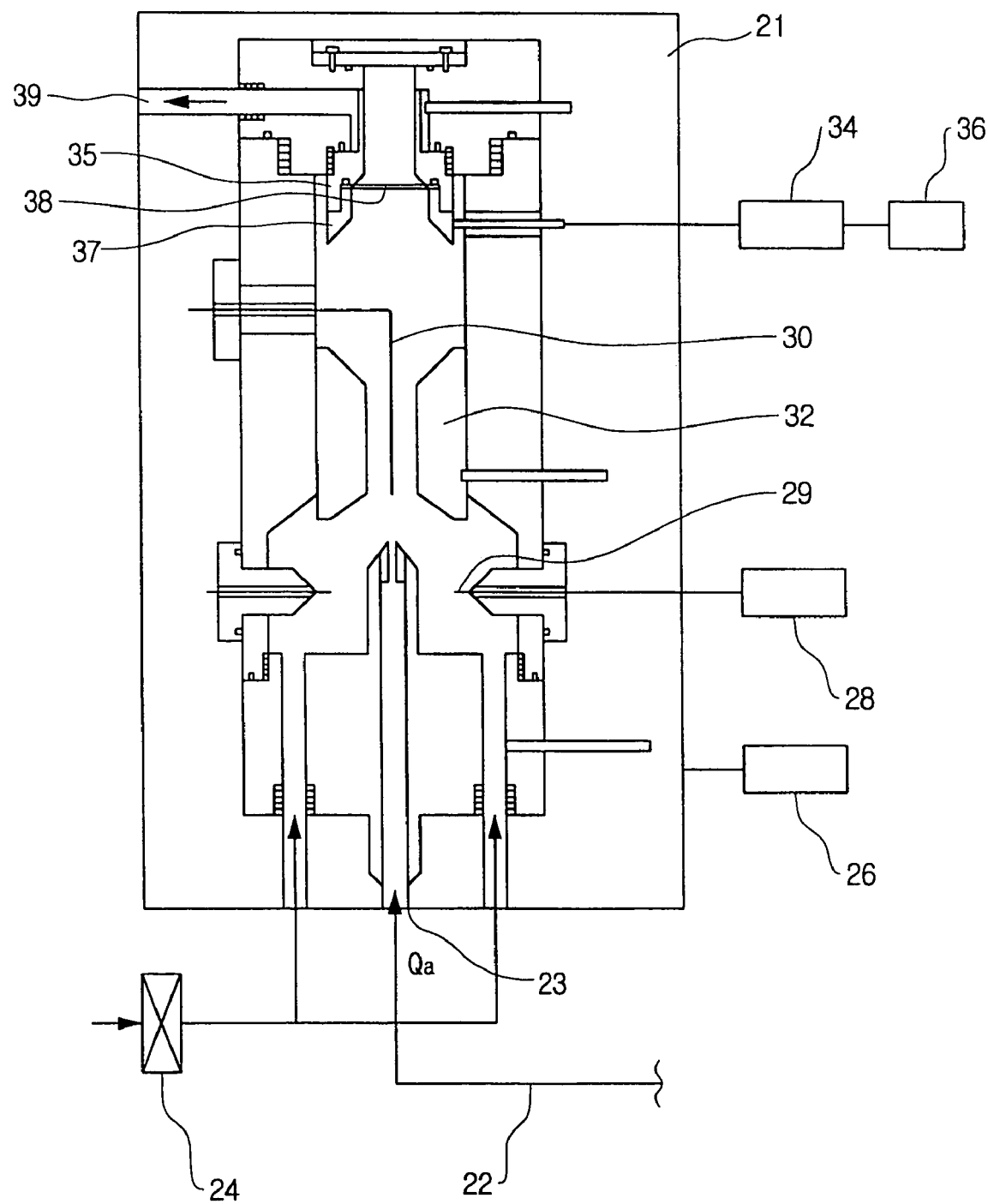
FIG. 2 is a view showing an electrical detection unit according to an embodiment of the invention.

FIG. 2 is a schematic view showing the electrical detection unit 20.

Referring to FIG. 2, the electrical detection unit 20 comprises a housing 21. The housing 21 is structured such that an inside thereof is electrically shielded. The housing 21 is connected at a side thereof with a supply line 22 extending from the saturator 10 (refer to FIG. 1), and through the supply line 22 the working liquid vaporized in the saturator 10, the air and the ultrafine particles flow in the housing 21.

In the housing 21 are formed a charging section and a current measuring section sequentially from an inlet 23 through which the vaporized working liquid, air and ultrafine particles flow in the housing 21. After the vapor of working liquid is condensed on the surfaces of the ultrafine particles having flowed in the housing 21 and thus a volume of the ultrafine particles grows to that of the micro particles, the grown micro particles are charged by the charging section and a charge quantity of the charged particles is measured by the current measuring section so as to calculate a number concentration of the ultrafine particles. Hereinafter, an internal structure of the housing 21 will be specifically explained in order.

A low temperature regulator 26 is mounted to a side of the housing 21 constituting a frame of the electrical detection unit 20 to maintain a temperature in the housing 21 to be constant. In this case, the temperature in the housing 21 is maintained to be lower than the temperature in the saturator 10 so that the vaporized working liquid is condensed on the surfaces of the ultrafine particles included in the air. Accordingly, an internal section of the housing 21 adjacent to the inlet 23 naturally forms a condensing section due to the low temperature. In other words, the vapor of working liquid having flowed in the housing 21 through the inlet 23 is condensed on the surfaces of the ultrafine particles included in the air due to the low temperature in the housing 21. The volume of the ultrafine particles becomes larger due to the condensation of the working liquid and grows to that of the micro particles.

According to another embodiment of the invention, when internal temperatures of the saturator 10 and the housing 21 are maintained to be 38° C. and 18° C., respectively, the ultrafine particles diluted to be a number concentration of about 360 particles/cm$^3$ are grown to have a diameter of 5 μm due to the condensation of working liquid. In this case, since a geometrical standard deviation of the grown micro particles is less than 1.3, it can be seen that the sizes of the grown micro particles are very uniform.

The micro particles having uniformly grown as described above are charged in the charging section. The charging section according to a preferred embodiment of the invention comprises a plurality of electrodes 29 protruding from an inner wall of the housing 21 toward a center thereof, and a high voltage power supply 28 applying a high voltage to the electrodes 29. A high voltage of 4 kV or more is applied to the electrodes 29 by the high voltage power supply 28 to generate a corona discharge, thereby producing many ions in the housing 21. In this case, as the higher voltage is applied, the more ions are produced. Accordingly, the micro particles having grown due to the condensation of the working liquid are charged by diffusion charging while being mixed with the ions produced from the electrodes 29 of the charging section.

In the mean time, if extra ions remaining in the air, which are not charged on the micro particles besides the ions charged on the micro particles, are measured in the current measuring section, it is difficult to accurately measure a number concentration of the ultrafine particles. Accordingly, it is required to remove the ions remaining in the air. Such extra ions are removed in an ion removing section.

The ion removing section is located between the charging section and the current measuring section in the housing 21. The ion removing section comprises a voltage power supply (not shown) mounted to a side of the housing 21, an ion trap electrode 30 located in the center of the housing 21 and generating electric field by the voltage applied by the voltage power supply, and an ion removing wall 32 mounted to the inner wall of the housing 21. When a voltage of 75V or more is applied to the ion trap electrode 30 by the voltage power supply, the extra ions remaining in the housing 21 are forced to be away from the ion trap electrode 30 by an electric force. In other words, the extra ions are forced to move toward the inner wall of the housing 21 away from the ion trap electrode 30 located in the center of the housing 21 by the electric force. In this case, since the ion removing wall 32 is mounted to the inner wall of the housing 21, the ions pushed out collide with the removing wall 32 and thus are removed. In the mean time, since the micro particles charged with the ions have a relatively large inertia compared to the pure ions, they flow to the current measuring section without collision with the ion removing wall 32 by the ion trap electrode 30.

The current measuring section is located next to the ion removing section. The current measuring section comprises a conductive filter 38 collecting the charged particles to separate the ions and the particles from each other, a support member 37 and a fixing member 35 for supporting the conductive filter 38 and a current measuring device 34 measuring a current of the ions retained on the charged particles collected by the conductive filter 38 and displaying the measured current with a computer 36.

The conductive filter 38 serves to collect the charged particles included in the air flowing in, to separate the ions from the particles and to transfer the separated ions to the current measuring device 34. Accordingly, the smaller apertures of the conductive filter 38, the smaller micro particles can be collected. According to an embodiment of the invention, a high efficiency particulate air (HEPA) filter is employed as the conductive filter. Using the HEPA filter, it is possible to collect 99.97% or more of all the particles having any sizes. The conductive filter 38 has preferably a thickness of 0.5 to 1 mm and a diameter of 30 to 37 mm. Like this, it is possible to decrease a whole volume of the housing 21 by using the small-sized filter.

The conductive filter 38 is fixed by the support member 37 and the fixing member 35 in the housing 21. In order to prevent current from flowing between the filter 38, the support member 37 made of metal and the housing 21, the fixing member 35 is made of an electrically insulating material. The fixing member 35 may be preferably made of an insulating material such as Teflon.

In the mean time, the current measuring device 34 measures a current induced by the ions collected by the filter 38 and thus measures a number concentration of the ultrafine particles included in the air with the measured current. The air having passed through the conductive filter 38 is discharged to the exterior via an air outlet 39.

A reference numeral 24 refers to an additional flow supply pipe which is connected to a separate saturator (not shown) to supply additional flow for generating more ions in the housing 21.

Figure 3:
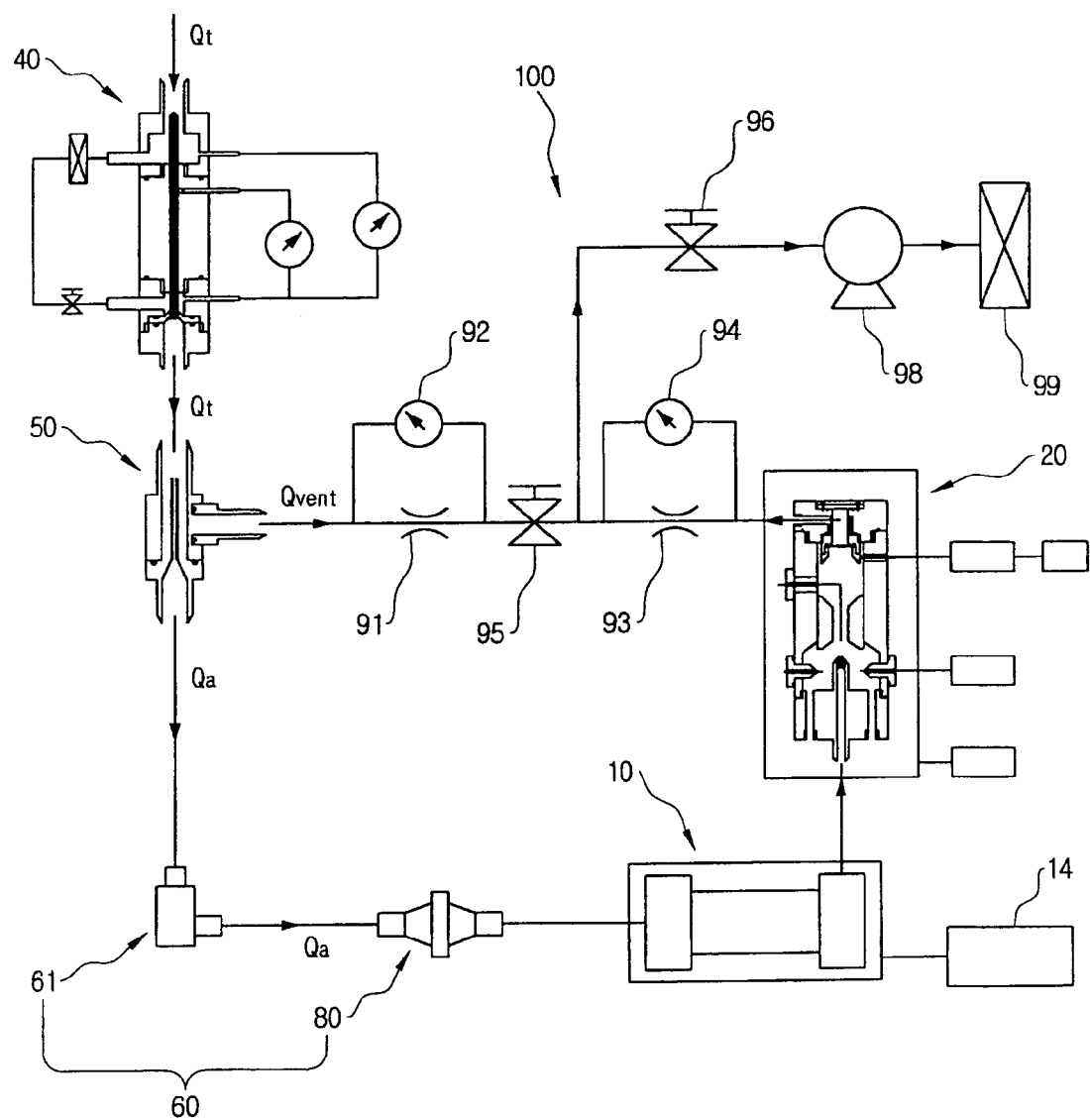
FIG. 3 is a schematic view showing a structure of a particle counter according to another preferred embodiment of the invention.

FIG. 3 is a schematic view showing a structure of a particle counter according to another embodiment of the invention.

Referring to FIG. 3, the particle counter according to this embodiment is different from the embodiment shown in FIG. 1. in that it further comprises a diluting device 40 inhaling air to dilute the number concentration of ultrafine particles contained in the air, a flow splitter 50 splitting an amount of the air just enough to be used for the measurement from the air diluted by the diluting device 40, and a particle separating unit 60 separating particles having sizes rather than a size to be measured from the air split by the flow splitter 50. Hereinafter, the constituting elements will be specifically explained with reference to Figs. It would be noted that the same reference numerals are used for the same members as the embodiment shown in FIG. 1.

Figure 4:
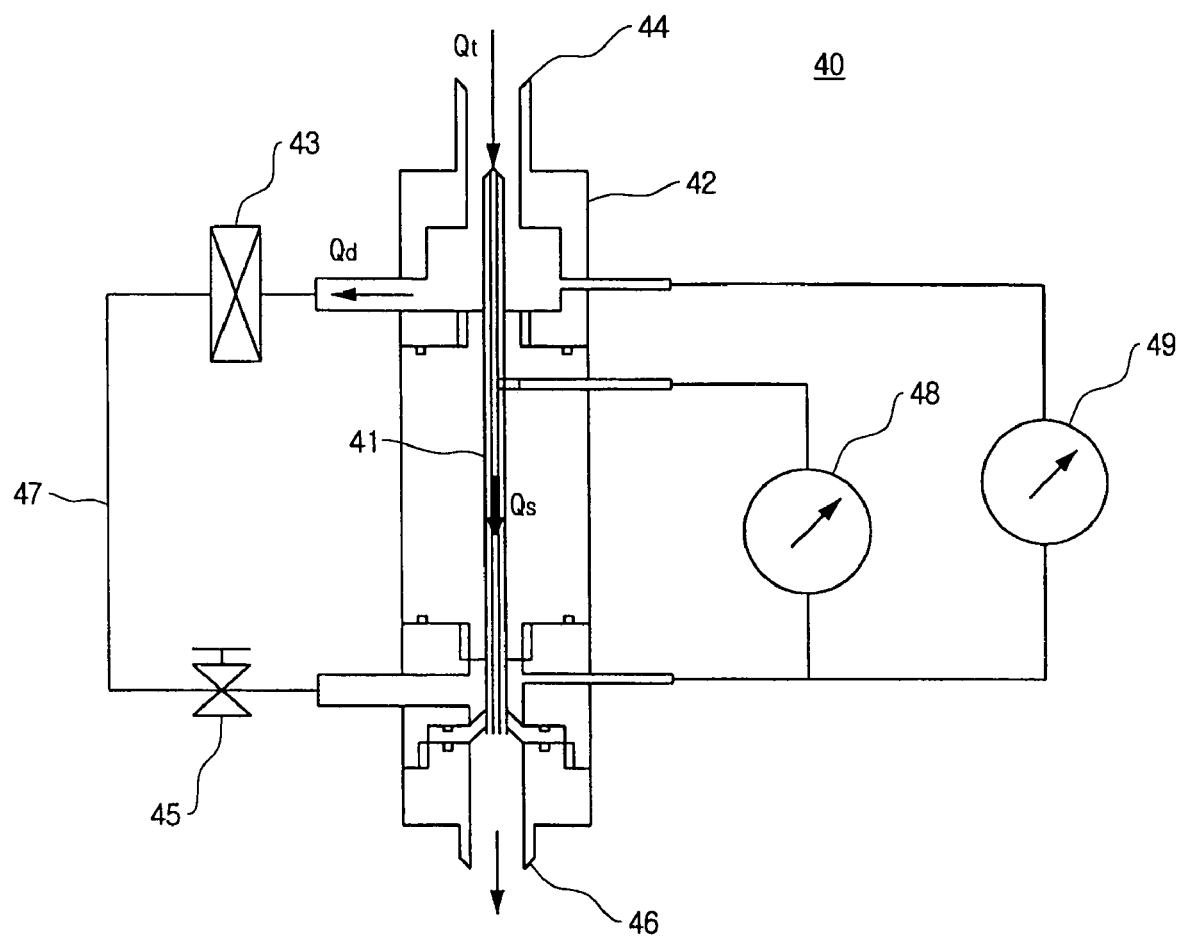
FIG. 4 is a schematic view showing a structure of a diluting device according to an embodiment of the invention.

FIG. 4 is a schematic view showing a structure of the diluting device 40 according to this embodiment.

Referring to FIG. 4, the diluting device 40 comprises a main body 42 having an air inlet 44 and an air outlet 46 formed thereto and a separate line 47 having a filter 43 and a regulating valve 45 provided thereto is formed to a side of the main body 42.

When the air with a flow rate of $Q_t$ flows in the main body 42 through the air inlet 44, some air with a flow rate of $Q_d$ flows through the separate line 47, and the residual air with a flow rate of $Q_s$ flows through an internal line 41 of the main body 42 as it does. The flow rate ($Q_d$) of the air flowing through the separate line 47 is subject to a removal of the particles with the filter 43 and then again converged into the main body 42. Accordingly, although a flow rate of the air to be discharged through the air outlet 46 is the same as the flow rate of inflow air, the particles of the flow through the separate line 47 are removed. As a result of that, the number concentration of the particles included in the whole air becomes low.

Like this, the reason to dilute a number concentration of ultrafine particles included in the air is that when the ultrafine particles are too many included in the air, the vapor of the working liquid generated in the saturator 10 (refer to FIG. 1) cannot be condensed on all the ultrafine particles and thus the ultrafine particles cannot grow to a uniform size thereof diameters of the grown particles may be diverse. Accordingly, in this embodiment, the number concentration of ultrafine particles of the inflow air are diluted to a certain degree, for example about 1/10 by the diluting device 40. In this case, the diluted number concentration of the ultrafine particles is measured by the electrical detection unit 20 (refer to FIG. 2) and the measured number concentration is multiplied by 10 to get the original number concentration of the ultrafine particles included in the inflow air.

In the mean time, the flow rate ($Q_d$) of an air flowing through the separate line 47 can be regulated by opening or closing the regulating valve 45. Specifically, as the regulating valve 45 is opened, the flow rate ($Q_d$) of the air flowing through the separate line 47 increases and thus the dilution ratio also increases. As the regulating valve 45 is closed, on the contrary, the flow rate ($Q_s$) of the air passing through the internal line 41 as it is without being filtered increases. A dilution ratio (D) is calculated by a following equation 1.

$$D = \frac{Q_t}{Q_s} = \frac{Q_d + Q_s}{Q_s} = 1 + \frac{Q_d}{Q_s} \qquad \text{[equation 1]}$$

According to an embodiment of the invention, it is possible to regulate the dilution ratio (D) up to 15 by adjusting the regulating valve 45 to regulate the flow rate ($Q_d$) of the air to be filtered.

According to an embodiment of the invention, manometers 48, 49 are provided to the diluting device 40 so as to accurately measure the flow rates of the air flowing through the internal line 41 and the separate line 47 of the diluting device 40. The first manometer 48 measures a pressure difference due to the flow in the internal line 41 in the main body 42 and the second manometer 49 measures a pressure difference due to the total flow in the main body 42. In this case, since there is a linear relation between the pressure difference ($\Delta$P1) measured by the first manometer 48 and the flow rate of the non-filtered air ($Q_s$), it is possible to structure a conversion table between the pressure difference ($\Delta$P1) and the flow rate of the non-filtered air ($Q_s$). Accordingly, the flow rate of the air to be filtered ($Q_d$) is independently determined by opening or closing the regulating valve 45 so as for the pressure difference ($\Delta$P1) to be the value corresponding to a desired flow rate of the non-filtered air ($Q_s$). In addition, an operator can check the total flow rate ($Q_t$) of the air flowing in the diluting device 40 by looking into the pressure difference ($\Delta$P2) of the second manometer 49 when the regulating valve 45 is completely opened.

Figure 5:
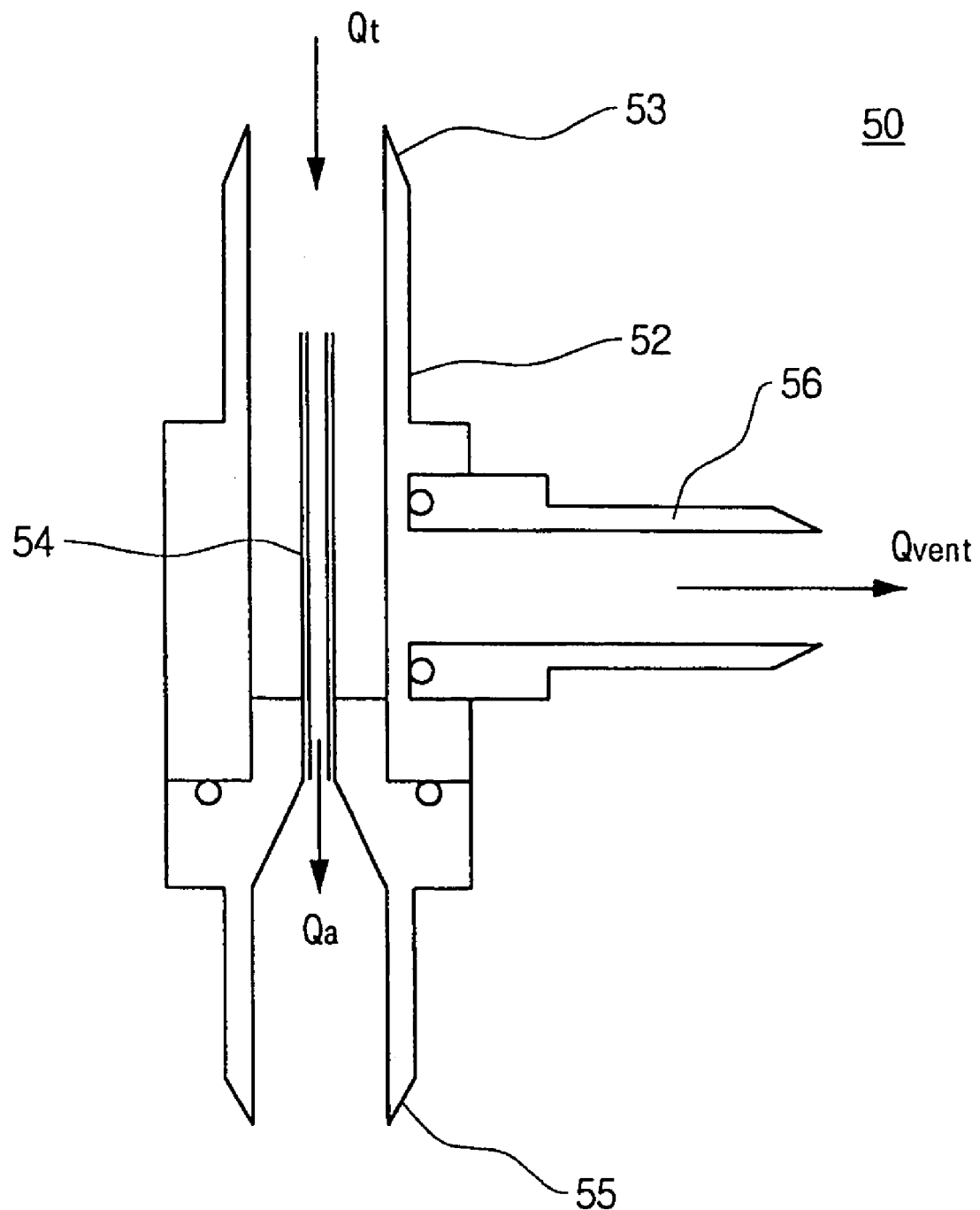
FIG. 5 is a schematic view showing a flow splitter according to an embodiment of the invention.

Referring to FIG. 3 again, the air diluted by the diluting device 40 flows in the flow splitter 50. FIG. 5 schematically shows the flow splitter 50.

Referring to FIG. 5, the flow splitter 50 comprises a body 52 having an air inflow passage 53, an air discharge passage 55 and a passage for vent line 56 formed thereto. In addition, the flow splitter 50 is connected to a flow rate regulating unit 100. The flow rate regulating unit regulates a flow rate of the air to be supplied to the particle separating unit 60 and a flow rate of the air to be discharged through the passage for vent line 56. In other words, air having an amount to be used for measurement of the air having flowed in the flow splitter 50 flows in the particle separation unit 60 through the air discharge passage 55 and the other residual air is discharged through the passage for vent line 56.

Specifically, a tube 54 having a predetermined diameter is mounted in the body 52. The air ($Q_t$) diluted in the diluting device 40 (refer to FIG. 4) flows in the body 52 of the flow splitter 50 through the air inlet passage 53.

Referring to FIGS. 3 and 5, the flow splitter 50 is designed such that the flow velocity of the air in the air inlet passage 53 and the flow velocity of the air in the tube 54 are the same. The flow rate of the air to be discharged through the passage for vent line 56 and the flow rate of the air passing through the air discharge passage 55 are regulated by the flow rate regulating unit 100. Meanwhile, as shown in FIG. 3, the flow rate regulating unit 100 comprises a first orifice 91 and a bypass valve 95 sequentially connected to the passage for vent line 56 of the flow splitter 50, a second orifice 93 connected to the air outlet 39 of the electrical detection unit 20, a flow rate regulating valve 96 connected to the bypass valve 95 and the second orifice 93, and a vacuum pump 98 and a filter 99 connected to the flow rate regulating valve 96.

The operator adjusts the flow rate regulating valve 96 to regulate an amount of the total air flowing in the particle counter according to the invention and opens/closes the bypass valve 95 to regulate the flow rate ($Q_{vent}$) to be discharged through the passage for vent line 56 of the flow splitter 50. As the vacuum pump 98 is driven, an exterior air flows in the diluting device 40 and the flow splitter 50. The air to be discharged through the vacuum pump 98 is filtered by the filter 99 to prevent the air pollution.

As described above, some flow rate ($Q_a$) of the air having flowed in the flow splitter 50 passes through the tube 54 and then is supplied to the particle separating unit 60 and the other air is discharged through the passage for vent line 56. In this case, the tube 54 in the body 52 is preferably shaped into a straight form having no bent regions. If a bent region is introduced to the tube 54, it is impossible to accurately measure an amount of the ultrafine particles in the air since the particles in the air collide with the tube 54 and thus are lost.

Referring to FIG. 3 again, the air split for the measurement in the flow splitter 50 flows in the particle separating unit 60. The particle separating unit 60 serves to remove particles having sizes rather than the size to be measured. According to the invention, the particle separating unit 60 comprises a maximum size particle separating device 61 removing particles having sizes larger than the size to be measured and a minimum size particle separating device 80 getting rid of particles having sizes smaller than the size to be measured.

Figure 6:
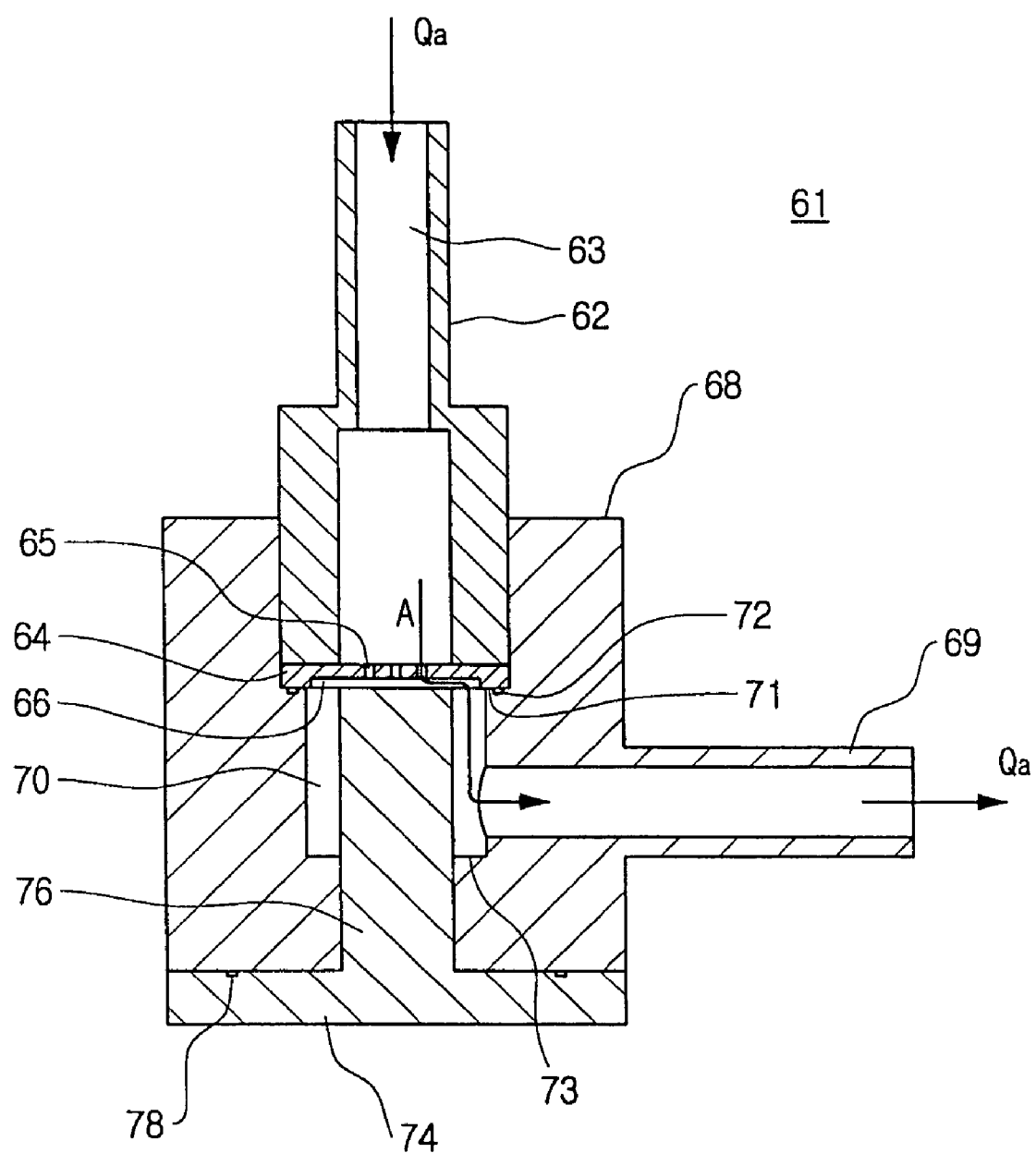
FIG. 6 is a cross sectional view of an impactor according to an embodiment of the invention.

According to the invention, an impactor is used as the maximum size particle separating device 61. FIG. 6 shows a cross section of the impactor.

Referring to FIG. 6, the impactor 61 comprises an air inflow member 62 having a hollow space 63 into which the air flows, a nozzle plate 64 located below the air inflow member 62 and having a plurality of nozzles 65, a body 68 having a hollow space 70 into which a lower end of the air inflow member 62 and the nozzle plate 64 are inserted through an end thereof, and a seal member 74 sealing the hollow space 70.

The air inflow member 62 has the hollow space 63 therein, so that the air split in the flow splitter 50 (refer to FIG. 5) flows into the space. The nozzle plate 64 includes the plurality of nozzles 65 formed at a center thereof and a concave part 66 formed on a lower surface thereof. The hollow space 70 formed in the body 68 is formed with engaging steps 71, 73 sequentially from an upper part thereof. The nozzle plate 64 is located on an upper surface of the first engaging step 71 adjacent to the upper part and the air inflow member 62 is positioned on the upper part of the nozzle plate 64.

In the mean time, the seal member 74 comprises a protruding part 76. The protruding part 76 is inserted into the hollow space 70 through the lower part of the body 68, so that the hollow space 70 is sealed. Since an inner diameter between the first and second engaging steps 71, 73 of the hollow space 70 is formed to be larger than an outer diameter of the protruding part 76, an air passage is spontaneously formed between the hollow space 70 between the first and second engaging steps 71, 73 and the protruding part 76. Meanwhile, an upper surface of the protruding part 76 is structured such that it is located on the same horizontal plane as the first engaging step 71 formed in the hollow space 70. In other words, the upper surface of the protruding part 76 and the nozzle plate 64 are located with being spaced apart as a height of the concave part 66. Reference numerals 72, 78 refer to seal rings that serve to prevent the outside air of the body 68 from flowing in.

A fluid flow in the impactor 61 having the structure as described above is as follows. The air ($Q_a$) split in the flow splitter 50 flows in the body 68 of the impactor 61 through the air inflow member 62. The air flowing in the hollow space 63 of the air inflow member 62 passes through the nozzle 65 at the nozzle plate 64 and then turns to 90° direction to pass through a space between the concave part 66 formed on the lower surface of the nozzle plate 64 and the upper surface of the protruding part 76 of the seal member 74, as indicated by an arrow A. Accordingly, the air flow having passed through the nozzle 65 turns to 90° direction due to the upper surface of the protruding part 76, and the particles having sizes larger than a certain size included in the air cannot come with the air flow due to the inertia, so that they collide with the upper surface of the protruding part 76 and thus are removed. Meanwhile, the air ($Q_a$) from which the particles having sizes larger than a certain size have been removed is discharged to the exterior of the impactor 61 through an outlet 69 formed on a side of the body 68.

With the above structure, the operator can regulate a maximum size of the particle to be removed by adjusting the number of the nozzles 65 formed in the nozzle plate 64 and the diameters of the nozzles 65. According to another embodiment of the invention, when three nozzles having a diameter of 0.3 mm are formed in the nozzle plate 64, it is possible to remove the particles having diameters larger than 0.3 μm and when one nozzle having a diameter of 0.9 mm is formed, it is possible to remove the particles having diameters larger than 1.0μm.

Figure 7:
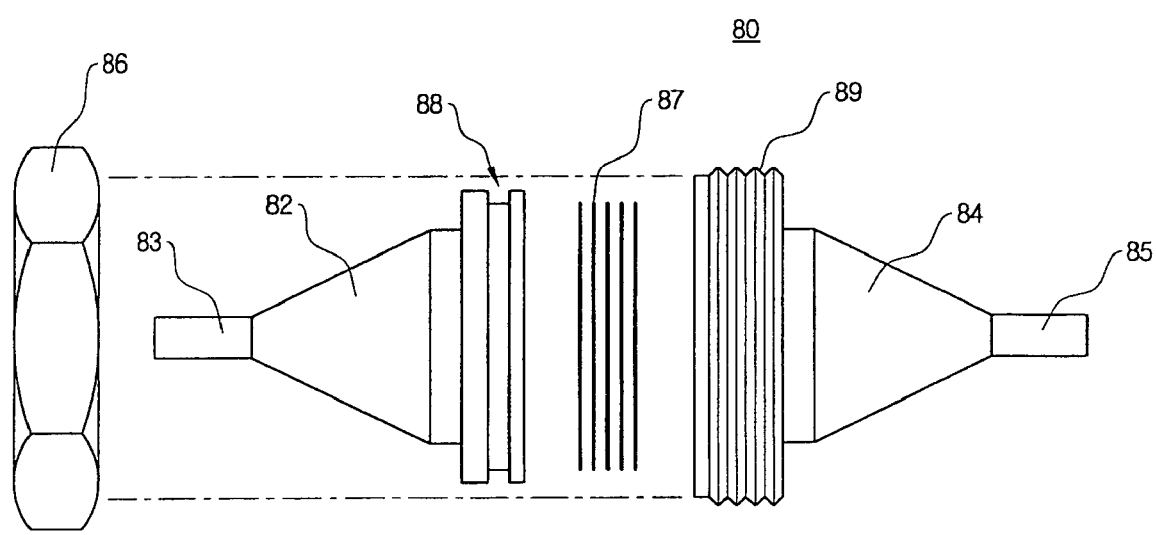
FIG. 7 is an exploded view showing a diffusion screen according to an embodiment of the invention.

The air having been discharged to the exterior of the impactor 61 flows in the minimum size particle separating device 80 (refer to FIG. 3) that separates the particles having a size to be measured or less. According to an embodiment of the invention, a diffusion screen is used as the minimum particle separating device 80. FIG. 7 is an exploded view of the diffusion screen 80.

Referring to FIG. 7, the diffusion screen 80 has an elliptic shape wherein a center thereof is more convex than an inlet 83 through which the air flows in, and comprises a first member 82 and a second member 84 which will be disassembled to right and left directions in FIG. 7. A plurality of screens 87 are mounted in the diffusion screen 80 perpendicularly to the direction of the air flow. A groove 88 formed at one end of the first member 82 is fitted with a seal ring (not shown) to prevent the exterior air from flowing in the diffusion screen 80 when the diffusion screen 80 is assembled. The one end of the first member 82 is inserted and fixed into the other end of the second member 84 and an engagement nut 86 is fitted to threads 89 formed on the other end of the second member 84, so that the first and second members 82, 84 are connected to each other.

With the above structure, the particles in the air having flowed in the inlet 83 make irregular Brownian motions in the diffusion screen 80. Meanwhile, displacement due to the Brownian motion is inversely proportional to the mass of the particle. Accordingly, the smaller the mass of a particle is, the larger the displacement amount by the Brownian motion is, and, on the contrary, the larger the mass of a particle is, the smaller the displacement amount by the Brownian motion is. Therefore, when the particles included in the air pass through the screens 87 installed in the diffusion screen 80, the particles having sizes smaller than a certain size collide with the screens 87 because the displacement amount by the Brownian motion is large due to the small mass, so that they are attached to the screens and thus removed. In the mean time, the particles having sizes larger than a certain dimension pass through apertures of the screens 87 as they are without colliding with the screens 87, since the displacement amount by the Brownian motion is small due to the large mass. According to another embodiment of the invention, when one screen is mounted, a minimum diameter of the particle passing through the screen is 0.015 μm and when five screens are mounted, a minimum diameter of the particle passing through all the screens is 0.052 μm. The air and the ultrafine particles having passed through the screens 87 flow in the saturator 10 (refer to FIG. 3) through an outlet 85.

Accordingly, the operator can easily regulate maximum and minimum diameters of the particle to be measured by the impactor 61 and the diffusion screen 80.

In the mean time, in the preferred embodiment of the invention, it has been described that all of the diluting device, the flow splitter and the particle separating unit are provided to the saturator and the electrical detection unit. However, it should be noted that the invention is not limited thereto and may have various combinations. For example, it is within the scope of the invention that the saturator and the electrical detection unit are further provided with the flow splitter only, the saturator, the electrical detection unit and the flow splitter are provided with the particle separating unit, and the saturator and the electrical detection unit are provided with the diluting device, the flow splitter and the particle separating unit.

As described above, according to the invention, it is possible to carry out a real time measurement of a number concentration of particles without using the optical sensor, and special attention is not needed in moving the equipment.

In addition, according to the invention, it is possible to easily measure the number concentration of the particles included in the air using the simple structure of the particle counter of the invention, compared to the prior art.

Additionally, according to the invention, the housing is made by integrating the condensing section in which the vapor of the working liquid is condensed on the surfaces of the ultrafine particles, the charging section in which the micro particles are charged, and the current measuring section measuring the current of the charged particles, and the internal temperature of the housing is maintained to be constant so that the working liquid condensed on the surfaces of the ultrafine particles in the air are not vaporized, thereby making it possible to measure the charge quantity of the charged micro particles more accurately.

While the invention has been shown and described with reference to certain preferred embodiments thereof, it will be understood by those skilled in the art that various changes in form and details may be made thereto without departing from the spirit and scope of the invention as defined by the appended claims.

What is claimed is:

1. A particle counter comprising:
  a saturator inhaling air in an atmosphere and vaporizing a working liquid therein; and
  an electrical detection unit electrically shielding an internal space thereof to maintain a temperature of the space to be constant, the air and vaporized working liquid flowing into the electrical detection unit through a side thereof from the saturator, condensing the vaporized working liquid on surfaces of ultrafine particles contained in the air, and charging the particles to measure a current of the charged particles, thereby measuring the number of the particles included in the air.

2. The particle counter as claimed in claim 1, the electrical detection unit comprises:
   a housing having an inlet through which the air and vaporized working liquid supplied from the saturator flow in and an inside to be electrically shielded;
   a low temperature regulator maintaining an inside temperature of the housing to be lower than that of the saturator inside and thus allowing the working liquid vaporized in the saturator to be condensed on the surfaces of the ultrafine particles included in the air;
   a charging section formed in the housing and charging micro particles having the working liquid condensed thereon; and
   a current measuring section formed in the housing and measuring a charge quantity of the micro particles charged in the charging section.

3. The particle counter as claimed in claim 2, wherein the working liquid is alcohol.

4. The particle counter as claimed in claim 2, wherein the charging section comprises:
   a plurality of electrodes protruding from an inner wall of the housing toward a center thereof; and
   a high voltage power supply applying a voltage to the electrodes, and
   wherein ions are generated in the housing by a corona discharge of the electrodes due to the voltage applied from the high voltage power supply and the micro particles having the working liquid condensed thereon are charged by the ions.

5. The particle counter as claimed in claim 4, further comprising an ion removing section positioned between the charging section and the current measuring section and removing residual ions which are not charged on the micro particles in the air.

6. The particle counter as claimed in claim 5, wherein the ion removing section comprises:
   a voltage power supply mounted to a side of the housing;
   an ion trap electrode located in the center of the housing and generating electric field by the voltage power supply to push the ions, which are not charged on the micro particles, toward the inner wall of the housing with an electric force; and
   an ion removing wall mounted to the inner wall of the housing and removing the ions having been pushed toward the inner wall of the housing.

7. The particle counter as claimed in claim 2, wherein the current measuring section comprises:
   a conductive filter collecting the charged particles to separate the ions and the particles from each other;
   a support member and a fixing member for supporting the conductive filter; and
   a current measuring device measuring a current of the ions retained on the charged particles collected by the conductive filter and displaying the measured current with a computer.

8. The particle counter as claimed in claim 7, wherein the conductive filter is a high efficiency particulate air (HEPA) filter.

9. The particle counter as claimed in claim 1, further comprising a flow splitter inhaling air in the atmosphere to split an amount of the air just enough to be used for measurement, and then supplying the split air to the saturator and discharging the residual air through a passage for vent line; and
   a flow rate regulating unit regulating a flow rate supplied to the saturator through the flow splitter and a flow rate discharged through the passage for vent line.

10. The particle counter as claimed in claim 9, wherein the flow rate regulating unit further comprises:
    a first orifice and a bypass valve sequentially connected to the passage for vent line of the flow splitter;
    a second orifice connected to an outlet of the electrical detection unit through which the air is discharge;
    a flow rate regulating valve connected to the bypass valve and the second orifice; and
    a vacuum pump connected to the flow rate regulating valve.

11. The particle counter as claimed in claim 9, further comprising a particle separating unit located between the flow splitter and the saturator and separating ultrafine particles which have sizes rather than a size to be measured from the air split by the flow splitter.

12. The particle counter as claimed in claim 11, wherein the particle separating unit comprises:
    a maximum size particle separating device removing particles having sizes larger than a size to be measured; and
    a minimum size particle separating device removing particles having sizes smaller than a size to be measured.

13. The particle counter as claimed in claim 11, further comprising a diluting device inhaling air in the atmosphere to dilute the number concentration of ultrafine particles contained in the air and supplying the diluted air to the flow splitter.

\* \* \* \* \*